(12) United States Patent
Reifman et al.

(10) Patent No.: US 8,977,349 B2
(45) Date of Patent: Mar. 10, 2015

(54) COLLECTION AND ANALYSIS OF VITAL SIGNS

(75) Inventors: Jaques Reifman, Fort Detrick, MD (US); Maxim Khitrov, Fort Detrick, MD (US); Andrew Reisner, Boston, MA (US); Liangyou Chen, Hanover Park, IL (US); Thomas McKenna, Frederick, MD (US)

(73) Assignee: The United States of America, as represented by The Secretary of the Army, Washington, DC (US)

( * ) Notice: Subject to any disclaimer, the term of this patent is extended or adjusted under 35 U.S.C. 154(b) by 0 days.

(21) Appl. No.: 13/429,036

(22) Filed: Mar. 23, 2012

(65) Prior Publication Data
US 2013/0076529 A1 Mar. 28, 2013

Related U.S. Application Data

(63) Continuation-in-part of application No. 13/204,657, filed on Aug. 6, 2011, now Pat. No. 8,694,085.

(60) Provisional application No. 61/401,179, filed on Aug. 6, 2010.

(51) Int. Cl.
*A61B 5/0432* (2006.01)
*G08C 19/00* (2006.01)
(Continued)

(52) U.S. Cl.
CPC ............... *G08C 19/00* (2013.01); *A61B 5/7221* (2013.01); *G06F 19/3418* (2013.01); *G06F 19/345* (2013.01); *G06F 19/3412* (2013.01);
(Continued)

(58) Field of Classification Search
USPC .................. 607/30, 31, 59; 600/513, 522–525
See application file for complete search history.

(56) References Cited

U.S. PATENT DOCUMENTS 5,425,373 A * 6/1995 Causey, III ..................... 600/510
5,683,432 A * 11/1997 Goedeke et al. ................. 607/32
(Continued)

FOREIGN PATENT DOCUMENTS

EP 1174816 A2 1/2002
WO 2010/035161 A1 4/2010

OTHER PUBLICATIONS

Chen, Liangyou, et al., "Algorithms to Qualify Respiratory Data Collected During the Transport of Trauma Patients," Physiological Measurement, 2006, pp. 797-816, vol. 27.
(Continued)

*Primary Examiner* — George Evanisko
(74) *Attorney, Agent, or Firm* — Elizabeth Arwine

(57) ABSTRACT

A system is disclosed having a storage, a communications module for interacting with a medical measurement device, an analysis controller, and a test module that allows for the testing and evaluating of decision-support algorithms. A method for testing decision-support algorithms is disclosed having the steps of receiving into storage of a ruggedized, compact computer at least one decision-support algorithm; detecting with a communications module the initiation of a vital-sign monitoring session; receiving and storing vital-sign information into storage by the communications module; pushing the stored vital-sign information by an analysis controller to a test module running the stored at least one decision-support algorithm; and providing at least one output from the decision-support algorithm to at least one of a database and a display.

17 Claims, 5 Drawing Sheets

(51) Int. Cl.
A61B 5/00 (2006.01)
G06F 19/00 (2011.01)
A61B 5/024 (2006.01)
A61B 5/0255 (2006.01)
A61B 5/145 (2006.01)

(52) U.S. Cl.
CPC ......... *A61B5/02416* (2013.01); *A61B 5/02438* (2013.01); *A61B 5/0255* (2013.01); *A61B 5/14542* (2013.01); *A61B 2560/029* (2013.01)
USPC ........................................................ 600/513

(56) References Cited

U.S. PATENT DOCUMENTS

| | | | |
|---|---|---|---|
| 6,182,245 B1 | 1/2001 | Akin et al. | |
| 7,222,265 B1 | 5/2007 | LeSuer et al. | |
| 7,251,454 B2* | 7/2007 | White | 600/300 |
| 7,899,687 B2 | 3/2011 | Morris | |
| 2002/0058861 A1 | 5/2002 | Drew | |
| 2005/0143671 A1* | 6/2005 | Hastings et al. | 600/513 |
| 2006/0111933 A1 | 5/2006 | Wheeler | |
| 2007/0094227 A1 | 4/2007 | Randazzo et al. | |
| 2008/0133275 A1 | 6/2008 | Haug et al. | |

OTHER PUBLICATIONS

Chen, Liangyou, et al., "Automated Beat Onset an Peak Detection Algorithm for Field-Collected Photoplethysmograms," 31st Annual International Conference of the IEEE EMBS, Sep. 2-6, 2009, pp. 5689-5692.
Chen, Liangyou, et al., "Can We Improve the Clincial Utility of Respiratory Rate As a Monitored Vital Sign?", Shock, Jun. 2009, pp. 574-580, vol. 31, No. 6.
Chen, Liangyou, et al., "Decision Tool for the Early Diagnosis of Trauma Patient Hypovolemia," Journal of Biomedical Informatics, 2008, pp. 469-478, vol. 41.
Chen, Liangyou, et al, "Diagnosis of Hemorrhage in a Prehospital Trauma Population Using Linear and Nonlinear Multiparameter Analysis of Vital Signs," Proceedings of the 29th Annual International Conference of the IEEE EMBS, Aug. 23-26, 2007, pp. 3748-3751, IEEE.
Chen, Liangyou, et al., "Exploration of Prehospital Vital Sign Trends for the Prediction of Trauma Outcomes," Prehospital Emergency Care, Jul./Sep. 2009, pp. 286-294, vol. 13, No. 3.
Chen, Liangyou, et al., "Exploiting the Existence of Temporal Heart-Rate Patterns for the Detection of Trauma-Induced Hemorrhage," 29th IEEE EMBS Annual International Conference, Aug. 20-24, 2008, pp. 2865-2868.
Dietterich, Thomas G., "Ensemble Methods in Machine Learning," First International Workshop on Multiple Classifer Systems, Oregon State University, 2000, pp. 1-15, vol. 1857.
Drew, Guy A., et al., "An Advanced Time Synchronized Multimedia Multiplatform Biomedical Data Acquisition System," United States Army Institute of Surgical Research, 2002.
Edmonds, Zachary V., et al., "The Reliability of Vital Sign Measurements," Annals of Emergency Medicine, Mar. 2002, pp. 233-237, vol. 39, No. 3.
Feeley, Mike, "US Army Institute of Surgical Research Data Acquisition System for Hemorrhage Moves to Next Phase." U.S. Army Medical Research and Material Command, http://www.kmimediagroup.com/mmt-home/251-mmt-2010-volume-14-issue-4-june/3001-us-army-institute-of-surgical-research-data-acquisiti... , vol. 14, issue 4, Jun. 2001.
Fishcher, Sandra, et al., "Handheld Computing in Medicine," Journal of the American Medical Informatics Association, Mar./Apr. 2003, pp. 139-149, vol. 10, No. 2.
Grinstead, Brad, et al., "Biomedical Signal Acquisition Using Labview," Proceedings of the 11th IEEE Symposium on Computer-Based Medical Systems, 1998, pp. 157-161.
Garner, Dainel C., et al., "Noise in Medical Helicopters," JAMA, Jul. 24/31, 1991, pp. 515, vol. 266, No. 4.
Jung Insung, et al., "User Pattern Learning Algorithm Based MDSS (Medical Decision Support System) Framework under Ubiquitous," World Academy of Science, Engineering and Technology 36 2007, 2007, pp. 184-188.
Kittler, J., et al., "Sum Versus Vote Fusion in Multiple Classifier Systems," IEEE Transactions on Pattern Analysis and Machine Intelligence, Jan. 2003, pp. 110-115, vol. 25, No. 1.
Koenig, Steven C., et al., "Integrated Data Acquisition System for Medical Devices Testing and Physiology Research in Compliance with Good Laboratory Practices," Biomedical Instrumentation & Technology, May/Jun. 2004, pp. 2-13.
Kramer, George C., et al., "Closed-Loop Resuscitation of Hemorrhagic Shock," UTMB, Anesthesiology Resuscitation Research Laboratory, Final Report, Feb. 21, 2011.
Kuncheva, Ludmila I., "A Theoretical Study on Six Classifier Fusion Strategies," IEEE Transactions on Pattern Analysis and Machine Intelligence, Feb. 2002, pp. 281-286, vol. 24, No. 2.
Lovett, Paris B., et al., "The Vexatious Vital: Neither Clinical Measurements by Nurses nor an Electronic Monitor Provides Accurate Measurements of Respiratory Rate in Triage," Annals of Emergency Medicine, Jan. 2005, pp. 68-76, vol. 45, No. 1.
Low, Ronald B., et al, "Accuracy of Blood Pressure Measurements Made Aboard Helicopters," Annals of Emergency Medicine, Jun. 1988, pp. 604-612, vol. 17, No. 6.
McKenna, Thomas M., et al., "The Physiology Analysis System: An Integrated Approach for Warehousing, Management and Analysis of Time-Series Physiology Data," Computer Methods and Programs in Biomedicine, Apr. 2007, pp. 62-72, vol. 86.
Musen, Mark A., et al., "Biomedical Infomatics: Computer Applications in Health Care and Biomedicine," 3rd Edition, 2006, pp. 698-736.
Norris, Patrick Roger, "Toward New Vital Signs: Tools and Methods for Physiologic Data Capture, Analysis, and Decision Support in Critical Care," Dissertation Submitted to the Faculty of the Graduate School of Vanderbilt University, May 2006.
Reifman, Jaques, et al., "Automated Decision-Support Technologies for Prehospital Care of Trauma Casualties," NATO RTO Human Factors & Medicine Panel Symposium, Use of Advanced Technologies and New Procedures in Medical Filed Operators, NATO OTAN, RTO-MP-HFM-182, Apr. 19-21, 2010, Essen, Germany.
Saleem, Mohammed, "Clincial Decision Support Systems," University of Connecticut, Computer Science and Engineering 300, May 5, 2008.
Tsien, Christien L., et al., "Poor Prognosis for Existing Monitors in the Intensive Care Unit," Critical Care Medicine, Apr. 1997, pp. 614-619, vol. 25, iss. 4.
Yu, Chenggang, et al., "A Method for Automatic Identification of Reliable Heart Rates Calculated form ECG and PPG Waveforms," Journal of the American Medical Informatics Association, May/Jun. 2006, pp. 309-320, vol. 13, No. 3.
National Instruments, "Options for Working with NI LabVIEW; The MathWorks, Inc. MATLAB Software; and M-File Scripts," NIWeek 2011, http://www.ni.com/analysis/matlab.htm.
Seeking Alpha, "Welch Allyn Adds Masimo Total Hemoglobin to Connex Vital Signs Monitors," Business Wire 2011, Jul. 14, 2011, http://www.seekingalhpa.com/news-article/1424024-welch-allyn-adds-masimo-total-hemoglobin-to-connex-vital-signs-monitor.

* cited by examiner

COLLECTION AND ANALYSIS OF VITAL SIGNS

This application is a continuation-in-part of U.S. patent application Ser. No. 13/204,657 filed Aug. 6, 2011, which claims the benefit of U.S. provisional patent application No. 61/401,179 filed Aug. 6, 2010 and entitled "System for Real-Time Collection and Analysis of Vital Signs and Prediction of Clinical Outcomes," which are hereby incorporated by reference.

I. FIELD OF THE INVENTION

This invention relates to a system and method for developing, testing, and evaluating decision-support algorithms in a portable unit using stored data and/or real-life, real time data.

II. BACKGROUND OF THE INVENTION

Typically, decision-support algorithms are incorporated into vital-sign monitors and other medical recording systems. This results in the algorithms being proprietary to the manufacturer and not facilitating easy modification or refinement by end-users and/or testing of new decision-support algorithms by either the manufacturer or the end-users.

Most of the existing literature discusses research in the decision-support area that uses retrospective analysis of previously gathered data to test and refine decision-support systems located on workstations and/or servers.

III. SUMMARY OF THE INVENTION

The invention provides in at least one embodiment a system for receiving an output from an external source where the system includes: a storage; a communications module for receiving vital-sign data from an external source and storing the received data in the storage; an analysis controller in communication with the storage, the analysis controller monitors the storage; a reliability module in communication with the analysis controller, the analysis controller includes means for determining whether the vital-sign data is quality vital-sign data; and a test module in communication with the analysis controller and the storage, the test module receives information from the storage through the analysis controller and stores any output in the storage, and the test module includes running means for running at least one algorithm loaded into the storage where the at least one algorithm processes at least a portion of the information provided by the analysis controller.

The invention provides in at least one embodiment a system for receiving vital-sign information from a vital-sign monitor, the system including: a storage having at least one database; a communications module for receiving vital-sign data from an external source and storing the received data in the database of the storage; an analysis controller in communication with the storage, the analysis controller monitors the storage; a reliability module in communication with the analysis controller, the analysis controller includes means for determining whether the vital-sign data is quality vital-sign data; a test module in communication with the analysis controller and the storage, the test module receives information from the storage through the analysis controller, and the test module includes running means for running at least one algorithm loaded into the storage where the at least one algorithm processes at least a portion of the information provided by the analysis controller, the running means provides an output in substantially real time from receipt of vital-sign data by the communications module; and a ruggedized, compact housing enclosing the storage, the communications module, the analysis controller, and the test module.

The invention provides in at least one embodiment a method for testing decision-support algorithms where the method includes: receiving into storage of a ruggedized, compact computer at least one decision-support algorithm; detecting with a communications module the initiation of a vital-sign monitoring session; receiving and storing vital-sign information into storage by the communications module; determining whether the vital-sign information is quality vital-sign information, when the vital-sign information is not quality then not using that vital-sign information; pushing the stored quality vital-sign information by an analysis controller to a test module running the stored at least one decision-support algorithm; and providing at least one output from the decision-support algorithm to at least one of a database and a display.

Given the following enabling description of the drawings, the invention should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements. The use of shading within the drawings is not intended as limiting the type of materials that may be used to manufacture the invention.

V. DETAILED DESCRIPTION OF THE DRAWINGS

FIGS. 1-4 illustrate different embodiments and aspects according to the invention.

In at least one embodiment, the system 100 is compact, which for this disclosure is defined as being easily moved and transported, for example, between a vehicle such as an ambulance or medical evacuation helicopter to a medical facility with the patient. Compact is further defined as smaller than a laptop and small relative to a vital-sign monitor 190 such as illustrated, for example, in FIG. 3. Compact is further defined by being of sufficiently small size to allow for use in the field away from established medical facilities.

In at least one embodiment, the system is ruggedized, which for this disclosure is defined as being able to substantially withstand vibration, shock, temperature, temperature shock, altitude, dropping, rain, dust, and humidity and remain substantially working and operational for its intended purpose.

In at least one embodiment, the system operates in real time, which for this disclosure is defined as storing and processing a continuous stream of vital-sign information (or data) as outputted by a vital-sign monitor where the processing includes any algorithm 1254 present in the test module 125 with substantially minimal lag time (e.g., allows for processing time by the algorithm(s) 1254). Examples of vital-sign information include heart rate, respiratory rate, arterial blood oxygen saturation ($SpO_2$), systolic and diastolic blood pressures, and mean arterial pressure.

Figure 1:
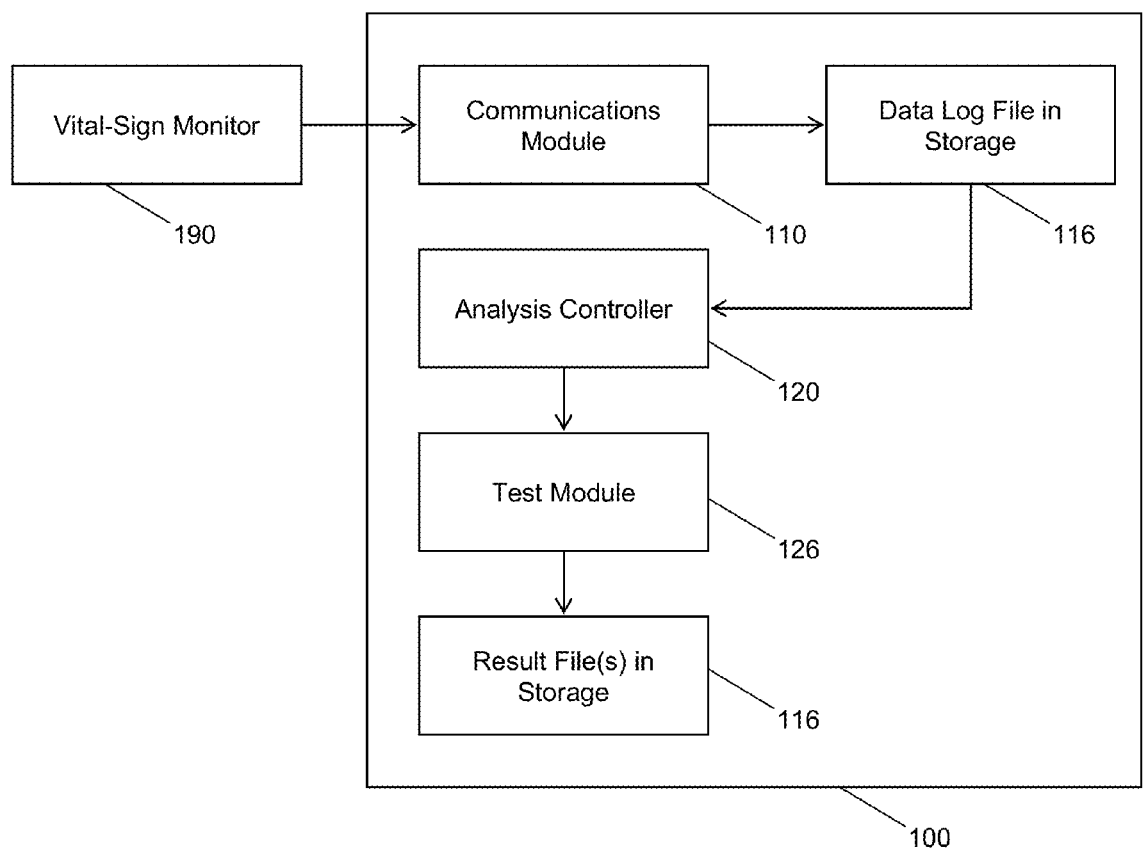
FIG. 1 illustrates a block diagram including a data flow according to an embodiment of the invention.

As illustrated in FIG. 1, the flow of data through at least one embodiment includes a system 100 having a communications module 110, a storage 115, an analysis controller 120, and a test module 125. The communications module 110 is in communication with the storage 115. The analysis controller 120 is in communication with the storage 115 and the test module 125, which in at least one embodiment is in communication with the storage 115. As used in this disclosure "in communication" includes physical and wireless connections that are indirect through one or more additional components (or over a network) or directly between the two components described as being in communication.

FIG. 1 also illustrates an example of how data will flow through at least one embodiment. The output of the vital-sign monitor (or other medical monitor or external source) 190 is received by the communications module 110 that stores the received data into storage (or memory) 115. In at least one embodiment, storage 115 includes a database for storing the received data. For the purposes of this disclosure, a database includes any type of list, data table, relational database, a text file, a comma delimited file, data log file, or a series of data files associated with one session. The analysis controller 120 monitors the storage 115 for the addition of new data that it will push to the test module 125. The test module 125 provides an environment in which a loaded algorithm(s) 1254 (illustrated in FIG. 2) operates to produce a result based on at least a portion of the data pushed by the analysis controller 120. The produced result in at least one embodiment is provided to at least one of the storage 115 including, for example, the database used for the received data or a separate database; a display 130; or for transmission to an external device through, for example, a wired connection or an antenna 1054 (illustrated in FIG. 3).

Figure 2:
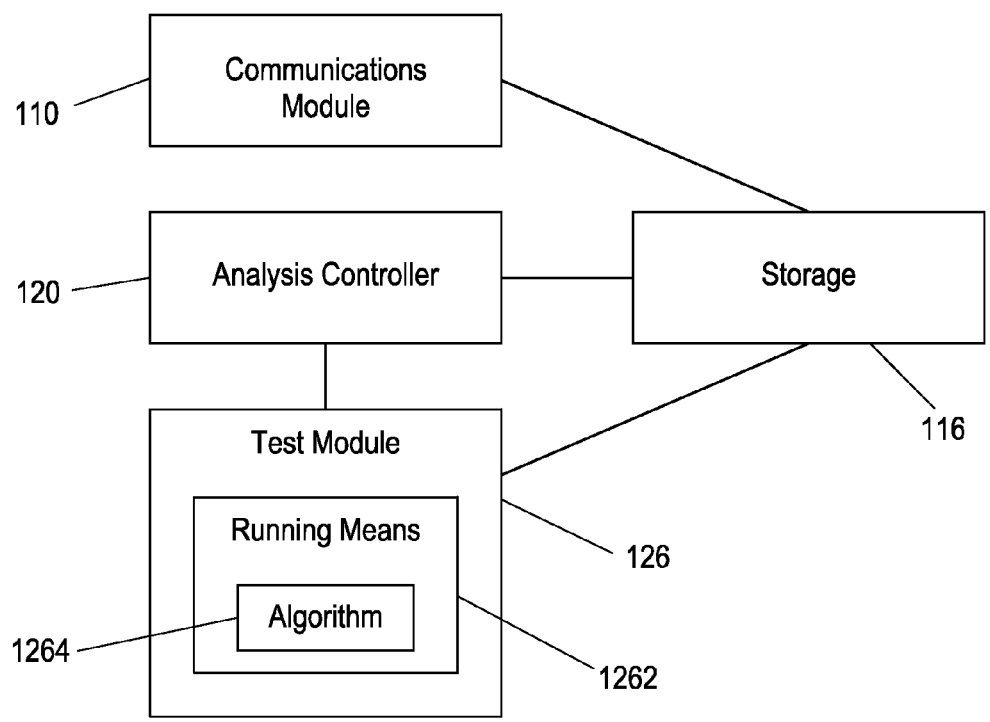
FIG. 2 illustrates a block diagram according to an embodiment of the invention.

FIG. 2 illustrates an embodiment similar to that of FIG. 1 without the flow of data being represented. FIG. 2 illustrates the system as including a communications module 110, a storage 115, an analysis controller 120, and test module 125.

The communications module 110 maintains the connection with the vital-sign monitor 190 and stores the received data (e.g., vital-sign information) into storage 115. The communications module 110 in at least one embodiment transmits a "keep-alive" (or similar) packet (or message) to the vital-sign monitor 190 to maintain the connection and avoid termination of the connection by the vital-sign monitor 190. The communications module 110 in at least one embodiment traps errors and recovers from communication errors using, for example, cyclic redundancy check to determine if corruption is present in the received packet of information. In addition in further embodiments, the communications module 110 uses a sequential packet number, which in at least one embodiment cycles through a set of numbers, present at the start of each packet to maintain the received packets in order prior to storage 115 of the received information, which is useful in a network environment with multiple paths between the vital-sign monitor and the communications module. For example, the Welch Allyn Propaq vital-sign monitors produce packets at different frequencies. Numerical data from the vital-sign monitor, such as heart rate, respiratory rate, blood oxygen saturation, and noninvasive systolic, diastolic, and mean blood pressures, are outputted at a frequency of 1 Hz (once per second). The electrocardiogram (ECG), photoplethysmogram (PPG), and impedance pneumogram (IP) are waveforms that are reported at 182 Hz, 91 Hz, and 23 Hz, respectively, and in at least one embodiment the packets are sent every 88 ms with each packet having 16, 8, and 2 data points, respectively. The communications module 110 stores these data packets as these packets are received and, if necessary, the communications module 110 arranges them in order prior to storing the data packets in the storage 115.

In at least one embodiment, the communications module 110 is in a standby state until it receives a numeric heart rate value greater than 10 beats per minute or between 10 and 350 beats per minute and ends a session when no such value is received for a 5-minute interval (although other time periods may be used), for example, any length of time in a range of 2 to 15 minutes (including the end points). The end of the session in at least one embodiment is based on a predetermined threshold of length of time (predetermined time threshold) of receipt values less than 10 beats per minute (predetermined vital-sign threshold). The requirement for a heart rate value indicative of life provides a reasonable basis to assume that the vital-sign monitor 190 is attached to a person. However, in alternative embodiments, another vital-sign such as $SpO_2$ is used to determine whether a patient is connected to the vital-sign monitor. In a further embodiment, a signal representing that a patient is connected or other status indication such as a "fault" state from ECG leads being cleared is provided by the vital-sign monitor 190 to the communications module 110 to indicate when a session has started and/or ended. The end condition reflects the case where the vital-sign monitor 190 is turned off or simply detached from the patient at the end of a medical session such as arrival at a medical facility. It is estimated that a one-hour session will require approximately 5 MB of disk space. In this embodiment, once the communications module 110 detects the start of a session, then it notifies and/or activates the analysis controller 120 and/or the test module 125 to start.

In a further embodiment, the communications module 110 timestamps the vital-sign information as part of storing the information into storage 115. The timestamp allows for improved archival of the information and for review of the information outputted by the test module 125, which in at least one embodiment allows for further refinement of the algorithm(s) 1254 operating in the test module 125.

The storage 115 in at least one embodiment is computer storage medium as defined later in this disclosure. An illustrative example of the storage 115 is a memory. Based on this disclosure, it should be appreciated that storage 115 also includes a plurality of discrete storages for the different data being stored in the system.

The analysis controller 120 monitors the physiological data logged into the storage 115 for the presence of new data in at least one embodiment. When new data are detected and/or a new session started, the analysis controller 120 pushes that data to the test module 125 by extracting the information from storage 115 and providing it in an appropriate syntax for use by the algorithm(s) 1254 operating in the test module 125.

In at least one embodiment, the analysis controller 120 converts the packet data into multiple constant-frequency row vectors. The vector in at least one embodiment has a length equal to the frequency multiplied by the time period (e.g., the example below has a vector length of 4). The analysis controller 120 aligns and/or shifts the data contained in the storage 115 to take into account any communication breaks and/ or missing data. For example if the storage 115 contains the following data where Seq represents the packet number (or sequence):
Time=0, Seq=100, Data=[HR: 80, $SaO_2$: 98]
Time=1, Seq=101, Data=[HR: 82]
Time=3, Seq=103, Data=[HR: 81, $SaO_2$: 97]
The analysis controller 120 converts the information into two vectors (one for heart rate (HR) and one for oxygen saturation ($SaO_2$)):
HR=[80 82 NaN 81]
$SaO_2$=[98 NaN NaN 97]
where NaN (Not a Number) is representative of missing data, which in this example Sequence 101 was missing $SaO_2$ and Sequence 102 was missing in its entirety (or lost). The missing data was filled in with NaNs (although other fillers could be used to indicate the missing data) to preserve a frequency of 1 Hz for the data.

In an example where the sampling by the analysis controller 120 is to occur at 5 seconds, but the packet (Sequence 104) has not been stored in the storage 115. The analysis controller 120 in at least one embodiment includes a time threshold beyond which it will consider the packet to be lost.

In at least one embodiment, the analysis controller 120 pushes the data based on a predetermined sampling period to reduce the load on the test module 125 based on the algorithms being run in the test module 125. For example, in at least one embodiment, the analysis controller 120 retrieves the current data every 5 seconds although the algorithm(s) 1254 running in the test module 125 uses data at approximately 2 minute intervals. In at least one embodiment, the analysis controller 120 is implemented as a processor programmed with a configurable shell.

The test module 125 hosts and runs at least one algorithm with examples of the algorithms including but not limited to the following functions: pattern recognition, generation of graphical displays, generation of text files, determination of data quality, prediction of patient outcome using for example artificial intelligence classifiers, analysis of time-series vital-sign data, etc. In at least one embodiment, the test module 125 includes running means 1252 for running the algorithm(s) 1254 such as a software environment running on a processor in which the code used to write the algorithm(s) is capable of functioning and interacting with the vital-sign information provided to it by the test module 125. The test module 125 retrieves at least one algorithm 1254 from storage 115 and runs it in response to data received from the analysis controller 120. In at least one embodiment, the analysis controller 120 and/or test module 125 restrict the frequency of data provided to the algorithm(s) 1254 to reflect the processing time required for the algorithm(s) 1254, which results in data being provided at predetermined time intervals with some data being ignored with the most recent values being used at the predetermined time intervals. By retrieving the algorithm(s) 1254 from storage 115, it allows for the algorithm(s) 1254 to be updated, modified, or changed by loading into the storage 115 the new/modified algorithm making it available for the next session.

The result produced by the algorithm(s) 1254 is provided by the test module 125 to at least one of the storage 115, the display 130, and an external device (not shown). In at least one embodiment, there are at least two algorithms running with the first algorithm reviewing the vital-sign information for quality control and providing a filtered output of the vital signs that pass quality control to the second or more algorithms running in the test module 125.

In at least one embodiment, the data placed into storage 115 is organized by session, which as used in this disclosure means a time period from when a patient is connected to a vital-sign monitor to the time that they are disconnected for a period longer than the predetermined time threshold discussed above from the vital-sign monitor.

The algorithms 1254 that are tested, evaluated and/or used in the above-described embodiments will need to use the data syntax used by the analysis controller 120. In at least one embodiment, the algorithm(s) 1254 will have as its respective input(s) at least a portion of the vital signs in a form that will be able to communicate with the analysis controller 120. In at least one embodiment, the test module 125 will discard vital signs not of interest to the algorithm(s) 1254; however, in other embodiments the test module 125 provides all vital signs received from the analysis controller 120 to the algorithm(s) 1254 with the algorithm(s) 1254 deciding what data it wants to use. In at least one embodiment, the test module 125 and the algorithm(s) 1254 are built using the same computer language or code such as MATLAB, C, or LabVIEW. In at least one embodiment, the test module 125 is a processor executing software to perform the functions described for the test module 125.

Figure 3:
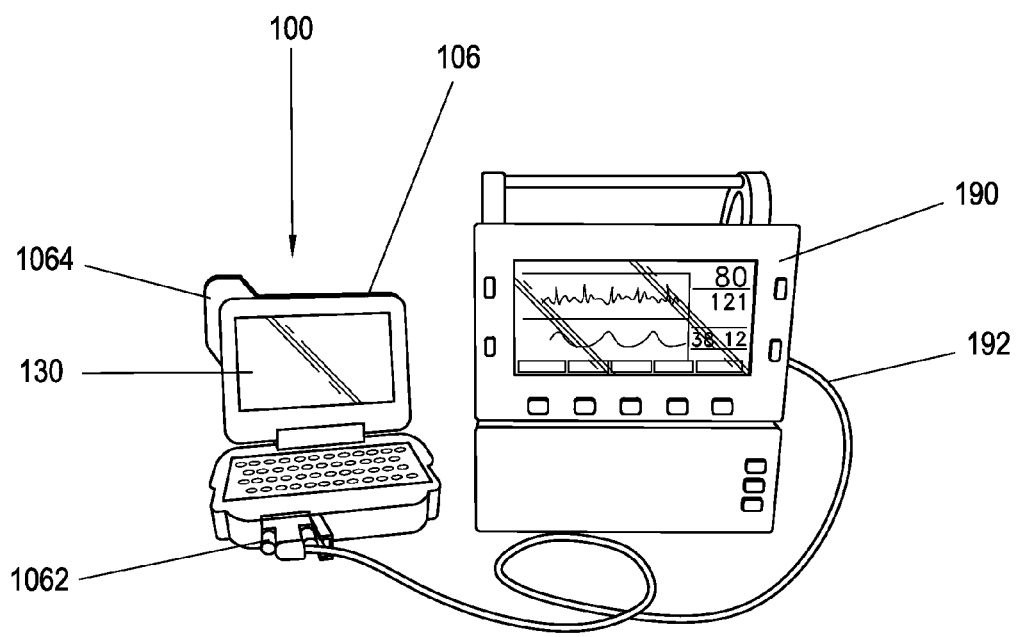
FIG. 3 illustrates an embodiment according to the invention.

FIG. 3 illustrates an example of an embodiment built according to the invention attached to a vital-sign monitor 190 such as the Propaq Encore sold by Welch Allyn although other vital-sign monitors could be used instead. There are a variety of ways for the system to communicate with a vital-sign monitor including but not limited to wireless or wired, such as a RS-232/USB cable adaptor or RS-232/serial cable adaptor 192. Based on this disclosure, it should be appreciated that there are a variety of additional ways that a vital-sign monitor 190 can be connected to the system besides the illustrated connector. FIG. 3 also illustrates an embodiment of the system including a display 130 and a housing 105 with a connector 1052. The illustrated system 100 was built with a test module 125 using MATLAB.

Figure 4:
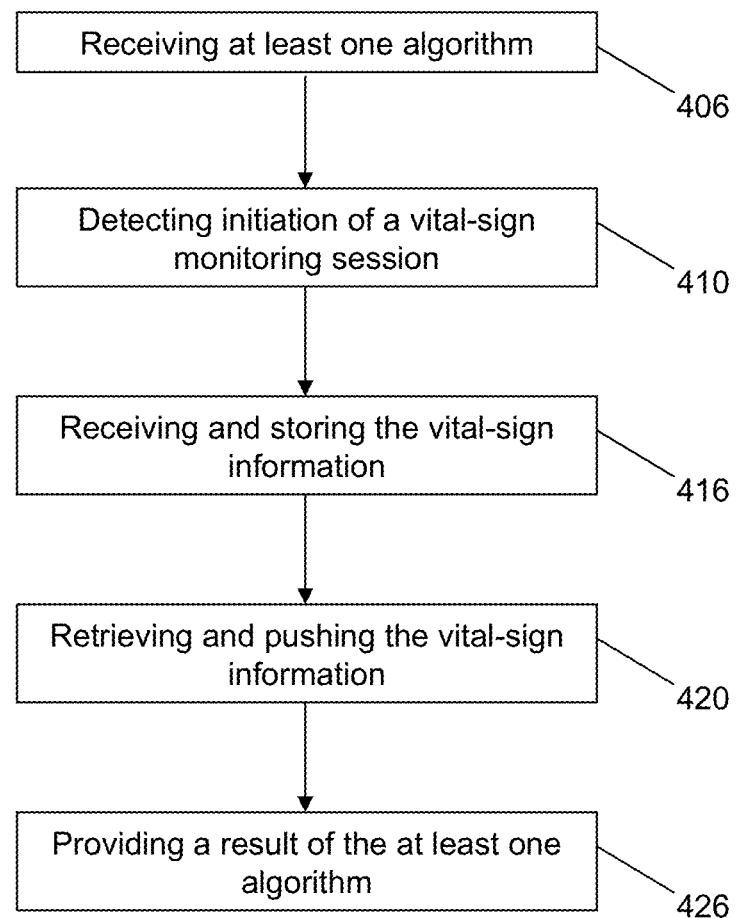
FIG. 4 illustrates a flowchart of a method embodiment according to the invention.

FIG. 4 illustrates a flowchart of a method embodiment according to the invention for using the system illustrated in FIG. 2. The illustrated method in at least one embodiment is for operation of at least one processor in a compact computer or a ruggedized, compact computer. In at least one embodiment prior to initiation of a session, the computer receives at least one algorithm into storage 115, 405. The algorithm(s) 1254 will be used by the test module 125 during a session. In at least one embodiment, the method includes detecting with the communications module 110 the initiation of a vital-sign monitoring session, 410. The communications module 110 receives and stores the vital-sign information into storage 115, 415. As discussed above in at least one embodiment, the analysis controller 120 retrieves the vital-sign information from storage 115 and pushes the vital-sign information to the test module 125 running the stored at least one decision-support algorithm 1254, 420. The test module 125 provides at least one output from the decision-support algorithm 1254 to at least one of a database 115 and a display 130, 425, or in an alternative embodiment to an external device by for example wireless transmission through an antenna 1054 of the output. In a further embodiment, the test module 125 outputs an audible alert when the algorithm(s) 1254 detects a critical condition or other predetermined situation. In a still further embodiment, the test module 125 retrieves the stored decision-support algorithm(s) 1254 from storage 115 after a session is initiated; or alternatively, the decision-support algorithm(s) 1254 is available in the test module 125 once received in storage 115.

In at least one embodiment, after multiple sessions are stored by the system, the stored data are transferred from the system for analysis and evaluation to determine whether the stored algorithm has functioned as intended and/or whether improvements should be made to the stored algorithm.

In at least one embodiment, the information captured by the system is stored or copied to a computer storage medium capable of removable form the system for transfer to the medical facility where the patient has been taken. Alternatively, this information is transmitted wirelessly to the medical facility.

Figure 5:
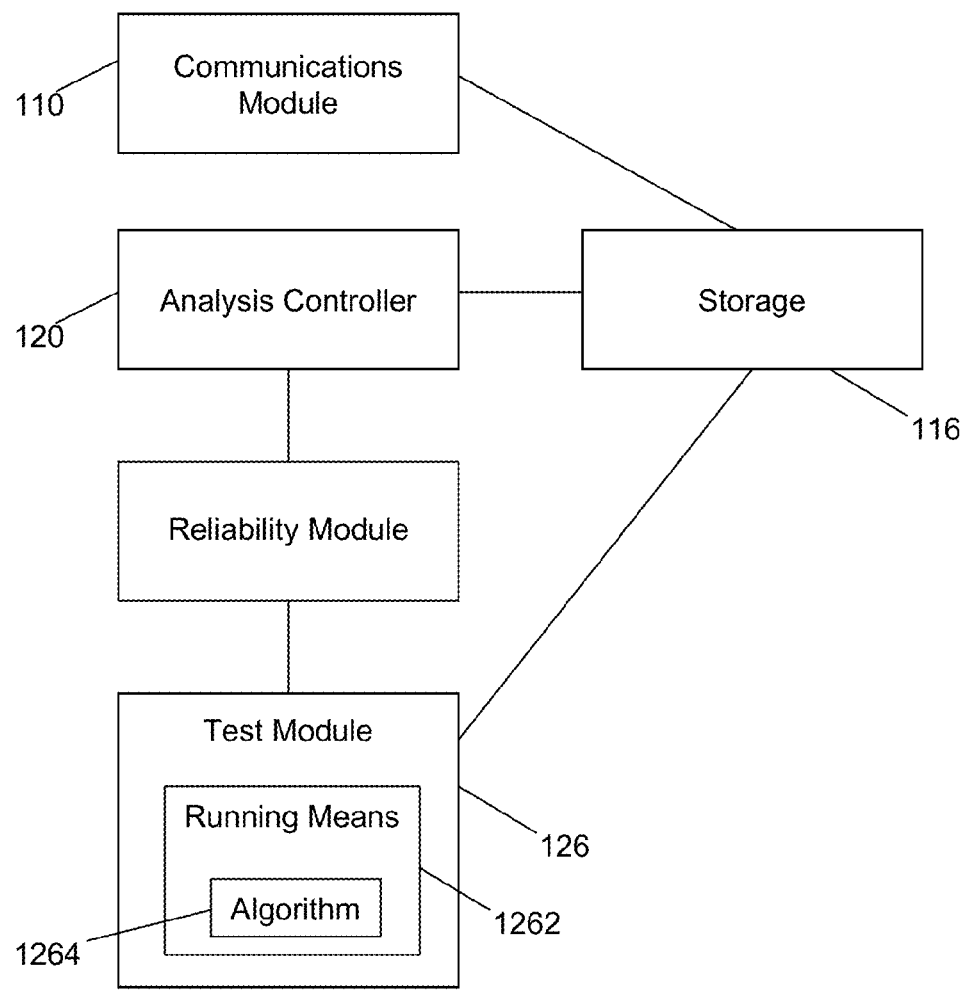
FIG. 5 illustrates a block diagram according to another embodiment of the invention.

FIG. 5 illustrates another embodiment according to the invention that adds a reliability (or preliminary data analysis) module 122 to the embodiment illustrated in FIG. 2. In a further embodiment, the reliability module 122 is combined with the analysis controller 120. In a further embodiment, the reliability module 122 is a module that is included in the test module 125 as another sub-module working in conjunction with the running means 1252 or as a quality control module discussed previously. In a further embodiment to any of the other embodiments, the reliability module 122 includes a library of modules to allow for better testing of the algorithm 1254 where each module is associated with at least one vital-sign reading. The reliability module 122 reviews the data provided by the analysis controller 120 to the test module 125 as part of a preliminary computation on the vital-sign data prior to use by the test module 125. In at least one embodiment, the reliability module 122 provides functionality that is important to a wide-range of different decision-support algorithms.

After the vital-sign information is acquired, the analysis controller 120 pushes the vital-sign information to the reliability module 122, which subsequently automatically determines when the vital-sign information appears to be accurately measured and/or likewise when the vital-sign information appears to be unreliable due to a measurement error. The determination of accuracy is made based on mathematical analysis of the vital-sign information performed on the vital-sign information over time. In at least one embodiment, the mathematical analysis employs methods that classify the vital-sign information on the basis of shapes as represented by a curve fit of the vital-sign information and/or the rhythmic and cleanness of waveforms that appear in the data time-series, periodicity of shapes that are identified in the data time-series, and on the degree of agreement between different mathematical algorithms that compute properties of the vital-sign information. In at least one embodiment, the decision-support algorithm 1254 being tested renders its computational decision on the basis of the vital-signs information that was determined to be reliable by the reliability module 122.

In a further embodiment, the reliability module 122 uses information for a second and/or third vital-sign to determine whether the information for the first vital-sign is reliable. For example, if two vital-signs are known to increase together or decrease together in patients, and when the vital-sign information for these two vital-signs are checked there is one increasing and one decreasing, then the reliability module 122 would identify both vital-signs as being potentially flawed. In a further embodiment, an additional check of both vital-signs information would be done to determine which of the two is flawed. Another example is if there are two sensors reading the same vital-sign, then when the vital-sign information from these two sensors disagrees and/or diverges, then it will be determined that one of the sensors is producing flawed vital-sign information.

The previous two paragraphs provide examples of means for determining whether the vital-sign data is quality vital-sign data where quality is defined as being sufficiently clean (or free) of noise and/or in agreement with at least one other vital-sign being monitored. In at least one embodiment, the quality means is a processor programmed to perform the analysis to determine whether the vital-sign information includes quality information.

In a further embodiment, a user of the system can readily adjust the functionality of the reliability module by, for example, adjusting the criteria for determining which vital-sign information is reliable can be made increasingly stringent or increasingly lenient.

As will be appreciated by one skilled in the art based on this disclosure, aspects of the present invention may be embodied as a system, method or computer program product. Accordingly, aspects of the present invention may take the form of an entirely hardware embodiment, a processor operating (or programmed) with a software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium is any tangible medium that can contain, or store, a program for use by or in connection with an instruction execution system, apparatus, or device. The above examples of computer readable storage medium are also examples of the storage of the above discussed embodiments.

Computer program code for carrying out operations for aspects of the present invention may be written in any combination of one or more programming languages, including an object oriented programming language such as MATLAB, Java, Smalltalk, C++, C#, Python, or the like and conventional procedural programming languages, such as the "C" programming language or similar programming languages. The program code in at least one embodiment executes entirely on the compact, portable computer as a stand-alone software package.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s) on at least one processor. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations or subcombinations of blocks in the block diagrams and/or flowchart illustration, can be implemented by special purpose hardware-based systems that perform the specified functions or acts, or combinations of special purpose hardware and computer instructions. These computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

Figure 6:
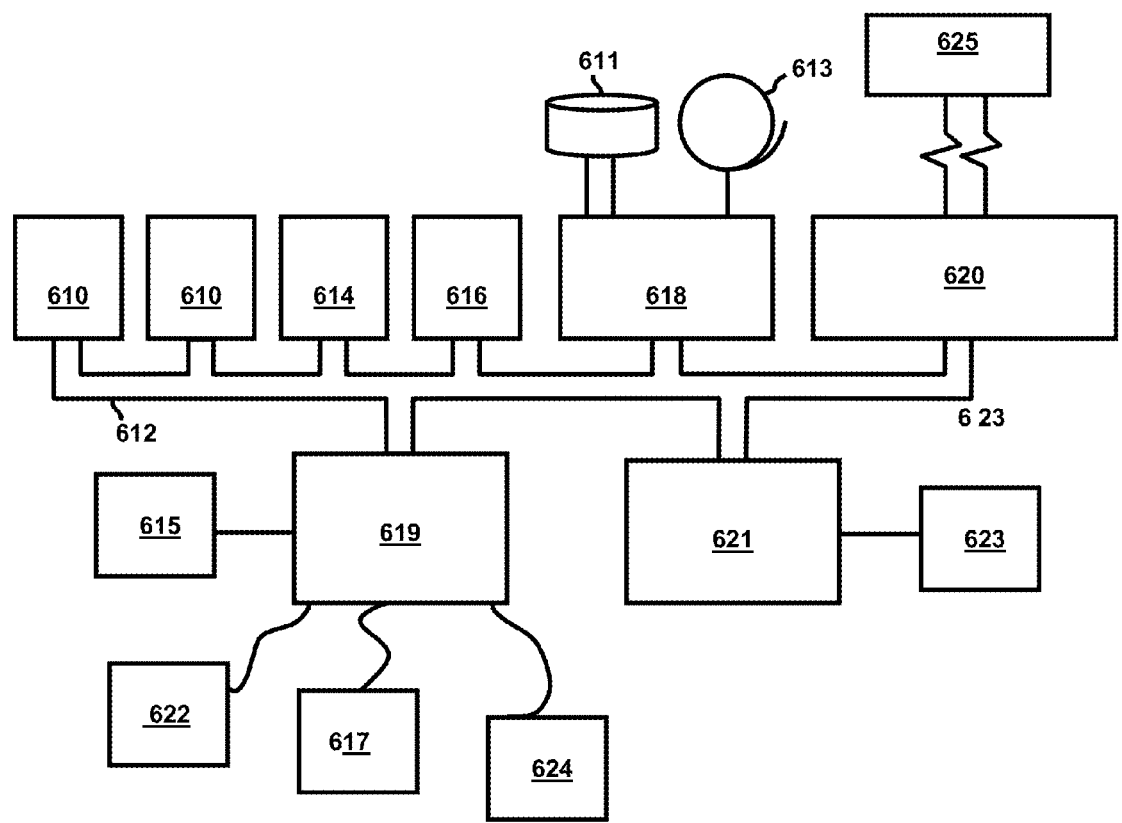
FIG. 6 illustrates a computer program product and computer implementation according to an embodiment of the invention.

FIG. 6 illustrates an example hardware environment for practicing at least one embodiment of the invention. This schematic drawing illustrates a hardware configuration of an information handling/computer system in accordance with at least one embodiment of the invention. The system includes at least one processor or central processing unit (CPU) 610. The CPUs 610 are interconnected with a system bus 612 to various devices such as a random access memory (RAM) 614, a read-only memory (ROM) 616, and an input/output (I/O) adapter 618. The I/O adapter 618 can connect to peripheral devices, such as disk units 611 and tape drives 613, or other program storage devices that are readable by the system. The system can read the inventive instructions on the program storage devices and follow these instructions to execute the methodology of at least one embodiment of the invention. The system further includes a user interface adapter 619 that connects a keyboard 615, a mouse 617, a speaker 624, a microphone 622, and/or other user interface devices such as a touch screen device (not shown) to the bus 612 to gather user input. Additionally, a communication adapter 620 connects the bus 612 to a data processing network 625, and a display adapter 621 connects the bus 612 to a display device 623, which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

We claim:

1. A method for testing decision-support algorithms comprising:
   receiving into a storage of a ruggedized, compact computer at least one decision-support algorithm;
   receiving and storing vital-sign information associated with a vital-sign monitoring session into the storage by a communications module;
   determining whether the vital-sign information is quality vital-sign information, when the vital-sign information is not quality vital-sign information then not using that vital-sign information;
   pushing the stored quality vital-sign information by an analysis controller to a test module running the stored at least one decision-support algorithm, wherein pushing includes
      retrieving the vital-sign information from the storage, and
      converting the vital-sign information into multiple constant-frequency row vectors; and
   providing at least one output from the decision-support algorithm to at least one of a database and a display.

2. The method according to claim 1, further comprising receiving the decision-support algorithm into the test module.

3. The method according to claim 1, wherein converting includes shifting data contained in the vital-sign information to leave gaps representing missing data.

4. The method according to claim 1, wherein the storage includes capacity for storing a plurality of decision-support algorithms, and
   the storage allows for quick exchange of stored decision-support algorithms.

5. The method according to claim 1, further comprising detecting with the communications module an initiation of the vital-sign monitoring session.

6. The method according to claim 5, further comprising determining when the vital-sign monitoring session has ended based on at least one of a vital-sign being less than a predetermined vital-sign threshold and a signal representing an end of the vital-sign monitoring session received from a source of the vital-sign information, and
   wherein detecting the initiation of the vital-sign monitoring is based on at least one of a vital-sign being above the predetermined vital-sign threshold and a signal representing a start of the vital-sign monitoring session received from the source of the vital-sign information.

7. A method for testing decision-support algorithms comprising:
   receiving into a storage of a ruggedized, compact computer at least one decision-support algorithm;
   receiving and storing vital-sign information associated with the vital-sign monitoring session into the storage by a communications module;
   detecting with the communications module an initiation of a vital-sign monitoring session;

determining whether the vital-sign information is quality vital-sign information, when the vital-sign information is not quality vital-sign information then not using that vital-sign information;

pushing the stored quality vital-sign information by an analysis controller to a test module running the stored at least one decision-support algorithm;

providing at least one output from the decision-support algorithm to at least one of a database and a display; and detecting when the vital-sign monitoring session terminates based on a received heart beats per minute being less than 10 heart beats per minute for a predetermined time threshold, and wherein detecting the initiation of the vital-sign monitoring includes detecting a heart beat per minute in excess of 10 heart beats per minute.

8. A method for testing decision-support algorithms comprising:

receiving into a storage of a computer at least one decision-support algorithm;

receiving and storing vital-sign information associated with a vital-sign monitoring session into the storage by a communications module;

pushing the stored vital-sign information by an analysis controller to a test module running at least one of the stored at least one decision-support algorithm, wherein pushing includes retrieving the vital-sign information from the storage, and converting the vital-sign information into multiple constant-frequency row vectors; and providing at least one output from the decision-support algorithm to at least one of a database and a display.

9. The method according to claim 8, wherein converting includes shifting data contained in the vital-sign information to leave gaps representing missing data.

10. The method according to claim 8, where the vital-sign information is received by the communications module from a vital-sign monitor; and wherein the computer is ruggedized and compact.

11. The method according to claim 10, further comprising loading at least one decision-support algorithm into the test module.

12. The method according to claim 10, wherein converting includes shifting data contained in the vital-sign information to leave gaps representing missing data.

13. The method according to claim 10, further comprising determining whether the vital-sign information is quality vital-sign information, when the vital-sign information is not quality vital-sign information then not using that vital-sign information.

14. The method according to claim 10, further comprising detecting with the communications module an initiation of the vital-sign monitoring session.

15. The method according to claim 14, further comprising determining when the vital-sign monitoring session has ended based on at least one of a vital-sign being less than a predetermined vital-sign threshold and a signal representing an end of the vital-sign monitoring session received from the vital-sign monitor, and wherein detecting the initiation of the vital-sign monitoring is based on at least one of a vital-sign being above the predetermined vital-sign threshold and a signal representing a start of the vital-sign monitoring session received from the vital-sign monitor.

16. The method according to claim 8, further comprising detecting with the communications module an initiation of the vital-sign monitoring session.

17. The method according to claim 16, further comprising determining when the vital-sign monitoring session has ended based on at least one of a vital-sign being less than a predetermined vital-sign threshold and a signal representing an end of the vital-sign monitoring session received from a source of the vital-sign information, and wherein detecting the initiation of the vital-sign monitoring is based on at least one of a vital-sign being above the predetermined vital-sign threshold and a signal representing a start of the vital-sign monitoring session received from the source of the vital-sign information.

* * * * *